United States Patent [19]

Streber

[11] Patent Number: 5,002,939
[45] Date of Patent: Mar. 26, 1991

[54] PHARMACEUTICAL COMPOSITION OF ESTER DERIVATVES OF HECOGENIN AND A METHOD OF USE IN THE TREATMENT OF BENIGN PROSTATA HYPERPLASIA

[75] Inventor: August S. Streber, Aichen, Fed. Rep. of Germany

[73] Assignee: Kanoldt Arzneimittel GmbH, Fed. Rep. of Germany

[21] Appl. No.: 434,344

[22] Filed: Nov. 13, 1989

[30]    Foreign Application Priority Data

Nov. 15, 1988 [DE]  Fed. Rep. of Germany ....... 3838716

[51] Int. Cl.$^5$ ............................................... A61K 31/58
[52] U.S. Cl. .................................................... 514/173
[58] Field of Search ........................... 514/173; 540/19

[56]    References Cited

U.S. PATENT DOCUMENTS 3,935,194  1/1976  Löken .................................... 540/18
4,265,886  5/1981  Pegel ..................................... 514/26

FOREIGN PATENT DOCUMENTS 582813  9/1959  Canada ................................... 540/19

*Primary Examiner*—Jerome D. Goldberg
*Attorney, Agent, or Firm*—Pravel, Gambrell, Hewitt, Kimball & Krieger

[57]    ABSTRACT

The invention concerns a pharmaceutical composition which comprises lower alkyl ester derivatives of hecogenin and pharmaceutically compatible carriers. The pharmaceutical composition has an inhibiting effect on cell growth and can be used for the causal treatment of benign prostata hyperplasia in human beings and in animals.

6 Claims, No Drawings

PHARMACEUTICAL COMPOSITION OF ESTER DERIVATVES OF HECOGENIN AND A METHOD OF USE IN THE TREATMENT OF BENIGN PROSTATA HYPERPLASIA

The invention concerns a pharmaceutical composition on the basis of hecogenin derivatives and a method of their use.

BACKGROUND OF INVENTION

Hecogenin, which is among the steroidal sapogenins (Merck index, Ninth Edition, 1976, p. 602) has been described in the glycosidally bonded form, in which the H atom of the OH group is replaced by a mono- or disaccharide group, for the inhibition of inflammation (DE-OS 29 26 463, DE-OS 27 59 171). The mono- or disaccharide groups can be partly or wholly esterified with monocarboxylic acids. A specially preferred compound from the series of glycoside derivatives of hecogenin is hecogenin-beta-D-glucoside and/or its ester. The inflammation inhibiting activity of the above-named compounds is based on inhibition of prostataglandine synthesis. The glycoside derivatives of hecogenin are described especially for the treatment of the accompanying inflammation processes, also for inflammation accompanying benign prostata hyperplasia. The aim of the treatment is the prostatitis which accompanies the benign prostata hyperplasia reactively and consecutively.

The named hecogenin derivatives, however, are not intended to treat benign prostata hyperplasia causally by inhibition of the cell growth and by reduction of the volume of the enlarged prostata.

For the alleviation and cure of benign prostata hyperplasia, until now nettle root extracts of urtica dioica, urtica urens and/or their hybrids have been used.

Like many natural products, these medicines are subject to qualitity fluctuations and they have a low content of the suspected active ingredient(s), so that by comparison with pure synthetic active substances a comparatively high dose is necessary.

OBJECT OF THE INVENTION

It is the object of the present invention to create a pharmaceutical composition. It should be usable, in particular, for the essential therapy in the urogenital zone. For preference it should not only alleviate the accompanying inflammation manifestations of benign prostata hyperplasia, but should also, based on the inhibiting effect of the cell growth, be able to achieve an improvement or cure in the benign prostata hyperplasia.

THE INVENTION

The above object is achieved in accordance with the invention by a pharmaceutical composition which comprises, as the pharmaceutically active substance, ester derivatives having the general formula (I) of hecogenin:

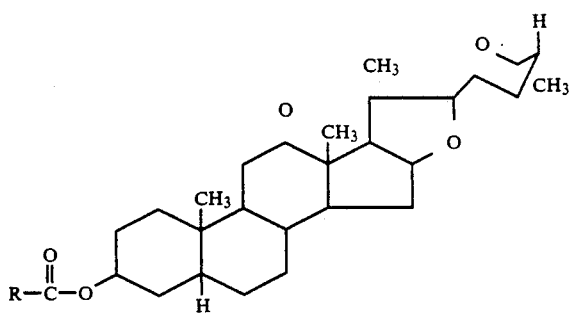

in which R is a $C_{1-4}$-alkyl radical and pharmaceutically compatible carriers. Thus in the formula above, R is a methyl, ethyl, propyl as well as a butyl group. These alkyl radicals may, if desirable, be substituted.

The synthesis of the compounds of general formula (I) can be performed in the conventional way by the esterification of the hecogenin with the corresponding acids. They can be processed in the manner known per se with the aid of suitable pharmaceutically compatible carriers to form powders, tablets, capsules, dragees, pills etc. for oral administration and to form emulsions or solutions for injection or infusion. The suitable dosing amount is preferably in the range from 3 to 30mg/kg body weight of the active substance per day, and the administration is done with advantage as long-term therapy or also as a quarterly treatment with the corresponding intervals.

The invention also comprises a method of use of hecogenin derivatives of the above general formula (I) for the treatment of benign prostata hyperplasia by administering a pharmaceutically effective amount thereof to human beings and mammals.

DESCRIPTION OF PREFERRED EMBODIMENT

In a preferred embodiment of the present invention, the pharmaceutical preparation contains as the pharmaceutically active substance hecogenin acetate ($R=CH_3$ in formula (I), which is a commercially available substance.

The invention will be described in more detail on the basis of the following results of investigation:

Test 1: in vivo investigations of the prostata volume

In a test series dogs suffering from benign prostata hyperplasia were given the inventive pharmaceutical preparation orally in the form of coated tablets over a period of 100 days. The daily dose was one coated tablet per 10 kg body weight, which contained as the active substance 5.0 mg hecogenin acetate. In accordance with the duration of the treatment, the decrease in the prostata volume was controlled by sonographic methods.

Test Group: Decline of Prostata Volume (%) after 100 days of treatment

| | |
|---|---|
| Dog 1 | 17.9 |
| Dog 2 | 60.1 |
| Dog 3 | 31.1 |
| Dog 4 | 4.9 |
| Dog 5 | 13.4 |
| Dog 6 | 87.8 |
| Dog 7 | 61.9 | average value: 39.6

The results above show clearly the high effectiveness of the inventive pharmaceutical preparation.

Test 2: Investigation of the Acute Toxicity of Hecogenin Acetate

The substance hecogenin acetate was investigated for acute oral and acute intraperitoneal toxicity on the NMRI mouse, the SPRD rat and the NZW rabbit.

The mice (both sexes, 23–25 g) and the rats (both sexes, 130–150 g) originated from a controlled SPF breed (breeder: IWF GmbH, 8192 Geretsried-Gelting), the rabbits (1.9 kg) came from the breeder Luise Brendt, 8710 Kitzingen.

The test animals were conventionally kept in artificially ventilated rooms (sterile air) at 20–21° C and 50–61 % relative air humidity in artificial light. The light/darkness change was made respectively after 12 hours, the air change ca. 10 times pre hour. The feeding was done ad lib. with the altromine standard diet, watering was ad lib. with mains water, which was partially softened and was periodically controlled microbiologically.

The mice and rats were kept in macrolene cages Type III, the rabbits were kept in Ebeco full wire cages.

The pretest stay of the animals was for 1 week.

| 1. | Acute oral toxicity testing | |
|---|---|---|
| | Test animals | NMRI mice |
| | Dose | 25 mg to 2.0 g/kg body weight |
| | Number of animals/dose | n = 10 (5 m + 5 f) |
| | Application volume | 40 ml/kg body weight uniformly |
| | Test animals | SPRD rats |
| | Dose | 25 mg to 2.0 g/kg body weight |
| | Number of rats/dose | n = 10 (5 m + 5 f) |
| | Application volume | 40.0 ml/kg body weight uniformly |
| 2. | Acute intraperitoneal toxicity testing | |
| | Test animals | NMRI mice |
| | Dose | 0.1 to 50 mg/kg body weight |
| | Number of animals/dose | n = 10 (5 m + 5 f) |
| | Application volume | 40.0 ml/kg body weight uniformly |
| | Test animals | NZW rabbits |
| | Dose | 0.5 to 2.0 g/kg body weight |
| | Number of animals/dose | n = 2 |
| | Application volume | 40.0 ml/kg body weight uniformly |

Results

The test mice and rats showed no symptoms in the test for acute oral toxicity, given the doses administered. The maximal administered amount corresponds to about 140 g in human beings. In the acute intraperitoneal toxicity test as well no symptoms appeared either in the mice or the rabbits when using the administered doses. The maximal administered amounts correspond in human beings to ca. 35 g or 140 g. In the individual tests a $LD_{50}$ could not be detected respectively up to the maximal limit of the stated dosing. The substance proved to be only slightly toxic in the animals used and is accordingly to be classified as of lower toxicity under the Gefahrlichkeitsverordnung (Danger Regulations) BGBI 1487. Within the administered doses, there is no expectation of acute toxicosis. Accordingly in human beings as well toxicosis with amounts administered orally once of up to ca. 10 g are not to be anticipated.

Using the inventive pharmaceutical preparations, a product has been created on the basis of ester derivatives of hecogenin, which due to the inhibition of the cell growth, makes possible causal treatment of benign prostata hyperplasia, which can be used in very small quantities, and is to be viewed as non-toxic.

As an example the production of a pharmaceutical preparation is described, with hecogenin acetate as the active ingredient, below:

EXAMPLE: Pharmaceutical preparation

The following substances were mixed in a ball mill and then pressed using an 8 mm coated pill stamp:

| | |
|---|---|
| hecogenin acetate | 10.00 mg |
| lactose | 134.00 mg |
| Ca- carboxymethylcellulose | 30.00 mg |
| Avicel ® | 10.00 mg |
| talc | 15.00 mg |
| Mg stearate | 1.00 mg |
| | 200.00 mg |

What is claimed is:

1. A method of decreasing the volume of the prostate in a mammal suffering from prostata hyperplasia comprising administering to said mammal an effective amount of a composition comprising
   (i) as the pharmaceutically effective substance an ester derivative of hecogenin having the general formula (I)

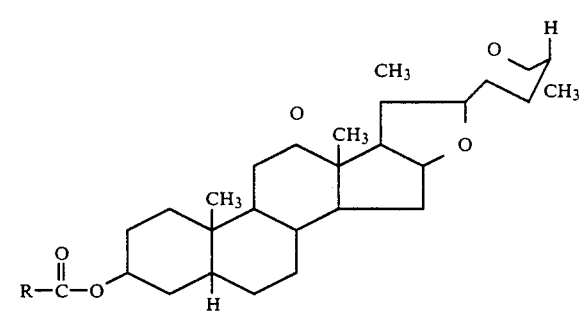

wherein R is a $C_1$–$C_4$ alkyl radical; and
   (ii) a pharmaceutically compatible carrier.

2. The method of claim 1, wherein said composition is administered orally.

3. The method of claim 2, wherein said composition is in the form of a powder, tablet, capsule, dragee, or pill.

4. The method of claim 1, wherein said composition is administered by injection or infusion.

5. The method of claim 4, wherein said composition is a solution or emulsion.

6. The method of claim 1, wherein R is selected from the group consisting of methyl, ethyl, propyl and butyl.

* * * * *